United States Patent [19]

Jacobs

[11] 4,436,754

[45] Mar. 13, 1984

[54] DISINFECTING AND STERILIZING COMPOSITION

[75] Inventor: Paul T. Jacobs, Arlington, Tex.

[73] Assignee: Surgikos, Inc., Arlington, Tex.

[21] Appl. No.: 343,678

[22] Filed: Jan. 28, 1982

Related U.S. Application Data

[63] Continuation-in-part of Ser. No. 178,218, Aug. 14, 1980, abandoned.

[51] Int. Cl.$^3$ ............................................. A01N 35/00
[52] U.S. Cl. ..................................... 424/333; 424/334
[58] Field of Search ......................................... 424/333

[56] References Cited

U.S. PATENT DOCUMENTS

| | | | |
|---|---|---|---|
| 3,016,328 | 1/1962 | Pepper et al. | 424/333 |
| 3,282,775 | 11/1966 | Stonehill | 424/333 |
| 3,697,222 | 10/1972 | Sierra | 424/333 |
| 3,912,450 | 10/1975 | Boucher | 424/333 |
| 3,968,248 | 7/1976 | Boucher | 424/333 |
| 3,983,252 | 9/1976 | Buchalter | 424/365 |
| 4,093,744 | 6/1978 | Winicov et al. | 424/333 |
| 4,103,001 | 7/1978 | Schattner | 424/333 |

OTHER PUBLICATIONS

Boucher Repiratory Care, vol. 23, No. 11, pp. 1063–1072, (1978).

*Primary Examiner*—Leonard Schenkman
*Attorney, Agent, or Firm*—Michael Q. Tatlow

[57] ABSTRACT

An improved disinfecting and sterilizing composition having low odor and irritation potential is disclosed. The composition is an aqueous solution containing a 2 to 6 carbon atom dialdehyde and may also contain formaldehyde and a diol or monosubstituted diol of the formula $RO(CH_2CH_2O)_nCH_2CH_2OH$; where R is H or $CH_3$ and n is an integer from 1 to about 22. Such compositions may be employed at a wide range of pH, from pH2 to pH9.

10 Claims, No Drawings

DISINFECTING AND STERILIZING COMPOSITION

This application is a continuation-in-part of application Ser. No. 178,218 filed Aug. 14, 1980 now abandoned.

FIELD OF THE INVENTION

This invention relates to improved chemical sterilization and disinfecting solutions and more particularly to compositions containing saturated dialdehydes having from 2 to 6 carbon atoms and a water soluble compound of the formula $RO(CH_2CH_2O)_nCH_2CH_2OH$ where R is H— or $CH_3$ and n is an integer from 1 to about 22. Such compositions have low odor and irritation properties and have excellent sporicidal properties.

PRIOR ART

1. Pepper et al. U.S. Pat. No. 3,016,328, which teaches disinfecting with a sporicidal composition containing a C2 to C6 saturated dialdehyde, such as glutaraldehyde, and an alkalinating agent in either alcoholic solution, or in aqueous solution at above pH 7.4.
2. Stonehill U.S. Pat. No. 3,282,775, which teaches disinfecting with sporicidal compositions containing a C2 to C6 saturated dialdehyde, preferably glutaraldehyde, and a cationic surface active agent.
3. Sierra U.S. Pat. No. 3,697,222, which teaches both sterilizing by contacting the equipment to be treated with an aqueous acid glutaraldehyde solution at temperatures above 45° C. and also by simultaneously subjecting the above solution to sound energy.
4. Boucher U.S. Pat. No. 3,708,263, which teaches sterilizing at temperatures below 75° C. by contacting the equipment to be treated with an aqueous chemical solution (pH 2.0 to 8.5) containing glutaraldehyde and DMSO simultaneously with ultrasonic wave energy.
5. Boucher U.S. Pat. No. 3,912,450; U.S. Pat. No. 3,968,248; U.S. Pat. No. 3,968,250, which teach disinfection or sterilization compositions that contain nonionic and anionic surfactants with aqueous or alcoholic glutaraldehyde solutions. These systems can be used with ultrasonic radiation.
6. Winicov et al. U.S. Pat. No. 4,093,744, which teaches sporicidal compositions containing glutaraldehyde at pH 6.5 to pH 7.4, which may contain a detergent and also a monoaldehyde.
7. Buchalter U.S. Pat. No. 3,983,252, which teaches disinfectant compositions that contain a dialdehyde and an alkali metal salt of a hydrocarbon carboxylic acid in aqueous solution and optionally, an alcohol with up to seven carbon atoms and/or a diol with up to four carbon atoms, e.g., ethylene glycol, propylene glycol, and butylene glycol, and/or a triol, glycerol. The compositions are stated to have improved stability in the pH range of from 6.0 to 7.4.
8. Schattner U.S. Pat. No. 4,103,001 discloses a sterilizing composition which contains glutaraldehyde, a phenol and a metal phenate as active ingredients. The composition may also contain a humectant such as glycerol, propylene glycol or di-ethylene glycol. The presence of the phenol in the composition results in a composition with a very strong phenol odor.

Boucher in *Respiratory Care*, November 1978, Volume 23, No. 11, pages 1063-1072, indicates (pages 1066-67) that glutaraldehyde physically complexed with a nontoxic aqueous glycol has less odor.

The compositions containing dialdehyde and a simple glycol of the type disclosed by Buchalter and Boucher in the *Respiratory Care* publication have been found to have significantly reduced sporicidal activity compared to the same compositions not containing the glycol.

SUMMARY OF THE INVENTION

It has now been discovered that a sterilizing and disinfecting composition containing a dialdehyde having 2-6 carbon atoms can be made with low odor and irritation potential by including in such composition a diol or mono-substituted diol of the formula $RO(CH_2CH_2O)_nCH_2CH_2OH$, wherein R is H— or $CH_3$— and n is an integer from 1 to about 22. These compounds will be hereinafter referred to as diol additives. Such compositions do not evidence the reduction in sporicidal activity that is evidenced in similar compositions containing other diols such as ethylene glycol, propylene glycol, butylene glycol or triols such as glycerol. The disinfecting compositions of the present invention are employed as aqueous solutions as the molecular weight of the diol additive is such that the diol additive is soluble in water.

An explanation for the significant difference in the sporicidal activity of the compositions of the present invention, compared with the compositions of the prior art, may be explained in terms of the chemical reactions possible between the various structures of the diol additives and the dialdehyde, specifically glutaraldehyde, carbonyl functionality. Compounds containing hydroxyl groups in the 1,2 or 1,3 positions such as ethylene glycol or propylene glycol form stable cyclic acetals at acid pH values, e.g. pH 3.0-6. These acetals are also stable at a higher pH and do not dissociate to the free aldehyde. The net result of acetal formation is a reduced rate of glutaraldehyde vaporization and a reduced sporicidal activity.

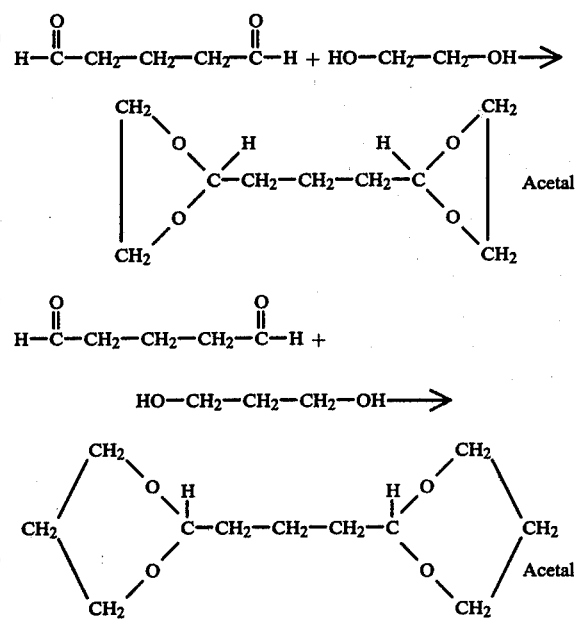

Polyethylene glycol compounds significantly reduce the rate of glutaraldehyde vaporization but do not inhibit the sporicidal activity of a solution containing glutaraldehyde. These compounds contain hydroxyl groups that can form hemiacetals with glutaraldehyde but do not have the proper structure to form a 5 or 6 membered cyclic acetal. For example:

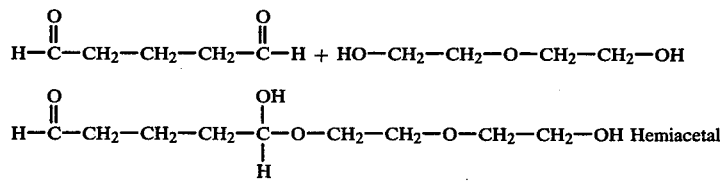

Hemiacetal formation apparently does not effect the sporicidal activity of the solution since at pH 7.5 the hemiacetal is unstable and remains in equilibrium with the free aldehyde and glycol. Acetal formation probably does not occur in these systems due to steric hinderance between the glycol and the hemiacetal (intermolecular acetal formation) and/or the unfavorable stability of the eight membered ring system formed in intramolecular acetal formation, e.g.:

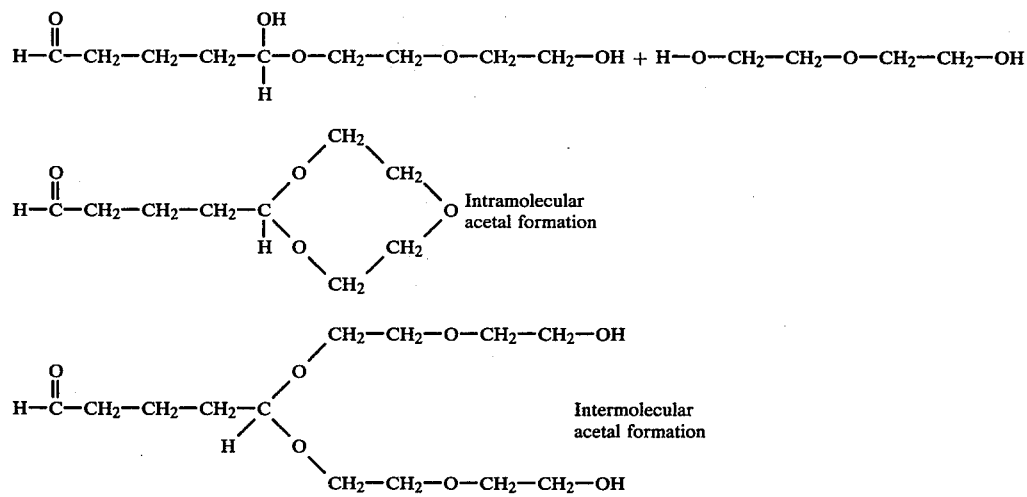

It is also evident from the following examples that the presence of the oxygen atom within the backbone of the molecule of the diol additives of this invention has a significant effect on the efficacy of the present compositions. Thus, diethylene glycol, $HOCH_2CH_2OCH_2CH_2OH$, does not reduce the sporicidal activity of the dialdehyde whereas 1,4 butanediol, $HOCH_2—CH_2—CH_2CH_2OH$, and 1,5 pentadiol, $HOCH_2CH_2CH_2CH_2CH_2OH$, do reduce the sporicidal activity of the dialdehyde. The presence of methyl groups on the backbone of the diol molecule also reduce the sporicidal activity of the dialdehyde in the composition. Thus, dipropylene glycol and tripropylene glycol reduce sporicidal activity but diethylene glycol and triethylene glycol do not.

The compositions of the present invention are employed in aqueous solutions containing a saturated dialdehyde and the diol additive as well as other ingredients such as pH buffers, corrosion inhibitors, stabilizers, fragrances, dyes, and surfactants.

The saturated dialdehydes which are known to have sporicidal activity are malonaldehyde, succinaldehyde, glutaraldehyde, adipaldehyde and oxaldehyde. The preferred dialdehyde is glutaraldehyde.

The compositions of the present invention may contain mixtures of the above-mentioned dialdehydes. In addition to the dialdehydes, the present compositions may also contain a monoaldehyde such as formaldehyde or acetaldehyde. The monoaldehydes, although known to have effective sporicidal activity, have not been extensively used in disinfecting and sterilizing solutions because of their strong odor and irritation. In the present compositions, the monoaldehydes can be employed in small amounts with a dialdehyde because of the significantly reduced odor and irritation potential of these compositions. The concentration of the dialdehyde in the finished composition, that is, the composition as employed by the user, is from about 0.1 to 4% based on the weight of the total solution. Concentrations higher than 4% may be used if desired. The preferred concentration is from 2% to 3%.

The compositions of the present invention may be formulated in two or more parts which are combined immediately prior to use. The formulation of the composition into multiple parts extends the shelf life of the composition. The dialdehydes are more effective against bacterial spores at an alkaline pH. However, the dialdehydes also have a tendency to autopolymerize at an alkaline pH, thereby reducing the effective concentration of the dialdehyde in the composition. The dialdehyde can be formulated in an aqueous solution at an acid pH, and activated with alkalinating agent immediately prior to use, shifting the pH to the alkaline range. This procedure is disclosed in the previously mentioned Pepper et al U.S. Pat. No. 3,016,328.

The diol additive in the present composition has the formula $RO(CH_2CH_2O)_nCH_2CH_2OH$ where R is H— or $CH_3$— and n is an integer from 1 to about 22. The specific compounds of the formula include diethylene glycol, triethylene glycol, polyethylene glycol, and methoxy polyethylene glycol. In the formulation of aqueous solutions of the present composition, the diol must be water soluble. The polyethylene glycols having a molecular weight below 1,000 (n in above formula=22) are water soluble.

The diol additive is present in the composition in an aqueous solution in an amount between about 5% and 25% based on the total weight of the solution with 20% being optimal. Concentrations higher than about 25% can be used but they do not result in any additional advantage.

An alkalinating salt is used in the composition as a buffer to maintain the proper pH of the composition in use. The alkalinating salt may be the type disclosed in the Pepper et al U.S. Pat. No. 3,016,328 which is an alkali metal carbonate or bicarbonate, e.g., sodium bicarbonate or potassium bicarbonate, or may be a phosphate, or hard water compatible borate. The buffer may also be an organic carboxylate salt such as sodium citrate, sodium acetate, potassium citrate or potassium acetate. The particular salt or mixtures of salts are present in a sufficient amount, 0.6% to 2.5% based on the total weight of the solution, to give the desired pH. The pH of the composition to obtain the optimum antimicrobial activity at room temperature is between pH 7.0 and 9.0.

The composition may contain other ingredients such as a surfactant, a corrosion inhibitor, a stabilizer for the aldehyde to inhibit polymerization, an antioxidant and dye or fragrance.

The composition of the present invention should not contain any other active or inactive ingredient which has a strong odor, as the presence of such an ingredient would defeat the purpose of the present invention. Examples of such ingredient which must be avoided are phenol and phenol-containing materials such as metal phenates which are disclosed in the previously mentioned Schattner U.S. Pat. No. 4,103,001. The presence of phenol not only provides a strong odor in itself but also increases the glutaraldehyde odor by increasing the glutaraldehyde vaporization. The present composition is free of phenol and phenol-containing materials.

A typical composition would contain the following ingredients. The percentages are by weight based on the total weight of the composition.

Glutaraldehyde: 2.5%
Polyethylene glycol 200 Molecular weight: 20%
Dipotassium Phosphate: 0.6%
Nonionic surfactant: 0.1%
Dye D&C Green No. 8: 0.001%
Distilled Water: Remainder The compositions of the present invention have a number of advantages over other sterilizing and disinfecting compositions. These include:

(a) the present compositions have significantly less odor and irritation potential than prior compositions;
(b) the sporicidal activity is not reduced;
(c) the compositions can be used as aqueous solutions;
(d) the compositions are effective at room temperature, 25° C., or at elevated temperatures, 30° C. to 50° C., without excessive odor;
(e) the compositions are effective over a very broad range of pH, pH 3 to pH 9.

In the following Examples, the test procedures employed to measure the aldehyde vapor content and the sporicidal activity are set forth below.

PROCEDURES FOR THE ANALYSIS OF ALDEHYDE VAPOR CONTENT REAGENTS

A 0.05% aqueous solution of 3-methyl 2-benzothiazolinone hydrazone hydrochloride (MBTH) was prepared fresh on the day of analysis.

An aqueous solution containing 1.6% sulfamic acid and 1.0% ferric chloride served as the oxidizing reagent of the MBTH solutions.

A saturated solution of 2,4 dinitrophenylhydrazine (2,4 DNP) in 2 N hydrochloric acid was prepared.

Chromotropic acid reagent was prepared by dissolving 0.33 g chromotropic acid in 100 ml of concentrated sulfuric acid.

PROCEDURE FOR THE ANALYSIS OF GLUTARALDEHYDE OR FORMALDEHYDE VAPOR BY MBTH

This procedure was used to determine the content of aldehyde which vaporized under room temperature conditions, that is 25° C., 55% humidity and ambient pressure (75.9 to 76.6 cm. mercury). A sampling train was devised as described below. Outside air was passed through a charcoal filter to remove particulate matter and carbonyls. The air flow was directed through a septum or serum sleeve-capped injection "T" through which 20 μl of the sample had been injected. The glutaraldehyde-enriched air was passed through a connected series of two fritted glass bubblers containing 75 ml and 15 ml of 0.05% MBTH respectively. After leaving the second scrubber, the volume of air flow was measured by a wet test meter followed by an air pump preset at a rate of 1.0 L/min. After 60 L of air was scrubbed, the pump was stopped and the scrubber solutions were individually transferred to appropriate volumetric flasks and diluted to volume with 0.05% MBTH. After one hour, 15 ml of the solutions were oxidized with 2.0 ml of the 1.0% ferric chloride/1.6% sulfamic acid solutions. Thirty minutes later, their absorbances were measured at 600 nm for glutaraldehyde and 625 nm for formaldehyde against a blank prepared from 15.0 ml of 0.05% MBTH and 2.0 ml oxidizing reagent. Their absorbances were compared to working standards ranging from 0.2 to 2 ppm aldehyde. Results were reported as ug aldehyde which vaporized. Percent recovery determinations accounted for 95 percent or more of the total aldehyde injected. Collection efficiency was good with 95 percent or more of the aldehyde trapped in the first scrubber.

When temperature and humidity conditions in the laboratory remained constant, precision was found to be ±10%.

To determine how much glutaraldehyde vaporized at 40° C., the entire apparatus excluding the wet test meter and pump was placed in an oven where the temperature was maintained at 40° C. The pump was turned on and the system allowed to equilibrate before the sample was injected, run and analyzed.

PROCEDURES FOR ANALYSIS OF GLUTARALDEHYDE, FORMALDEHYDE VAPOR MIXTURES

A sampling train was set up as outlined in the previous procedure except that the connected series of scrubbers was increased to three. Each scrubber contained 20 ml of distilled water. After 20.0 μl of the sample was injected, the pump was turned on and 60 L of air was pulled through. The solutions were removed from the scrubbers and the volume of each was adjusted to the original 20 ml with distilled water.

To determine glutaraldehyde concentration, 3.0 ml of the 2,4 DNP reagent was added to a 10 ml aliquot of each scrubber solution. After the solution was swirled to mix and allowed to sit for 3 minutes, the turbidity was measured at 640 nm against the 2,4 DNP reagent and was compared to that of known standards ranging from 2 to 10 ppm glutaraldehyde. No detectable glutaraldehyde was found after the first scrubber. Results were reported as μg glutaraldehyde which vaporized.

To determine the formaldehyde concentration in the solution, 5.0 ml of the chromotropic acid reagent was rapidly squirted onto a 5.0 ml aliquot of the test solution in such a way as to provide good mixing. The color was allowed to develop for eight minutes, was mixed on a vortex type mixer, and the absorbance was read at 570 nm against a blank prepared from 5.0 ml of distilled water and 5.0 ml of chromotropic acid. The absorbances were compared to that of standards representing 0.2 to 3 ppm formaldehyde. Slightly less than 95% of the formaldehyde was collected in the first scrubber. Results were reported as μg formaldehyde which vaporized. Percent recovery determinations accounted for 99 percent or more of the glutaraldehyde and formaldehyde injected.

SPORICIDAL TESTS

The sporicidal test employed in the Examples is the A.O.A.C. Sporicidal Test as specified in *Official Methods of Analysis* of the Association of Official Analytical Chemists (AOAC), 13th Edition, 1980, Sections 4.015–4.017.

EXAMPLE I

A series of solutions containing 2.5% by weight glutaraldehyde, 20% by weight of the compound indicated in Table I and water were aged for seven days at 40° C. Each sample was activated to pH 7.5 with 0.6% dipotassium phosphate and 1.7% potassium acetate. These activated solutions were tested for glutaraldehyde vaporization according to the test set forth above. The results are reported as relative percentages of glutaraldehyde vaporization, i.e., glutaraldehyde vaporized from a 2.5% glutaraldehyde solution containing 20% of the indicated compound divided by the glutaraldehyde vaporized from a 2.5% solution with no compound times 100.

TABLE I
Effect of Additives on Glutaraldehyde Vaporization

| Compound | % Glutaraldehyde Vaporization |
|---|---|
| None | 100 |
| Methanol | 81 |
| Ethanol | 107 |
| n-Propanol | 103 |
| Ethylene Glycol | 12 |
| 1,2-Propylene Glycol | 15 |
| 1,3-Propylene Glycol | 4 |
| 1,2-Butanediol | 3 |
| 1,3-Butanediol | 1 |
| 1,4-Butanediol | 6 |
| 1,5-Pentanediol | 12 |
| Glycerin | 8 |
| Sorbitol | 4 |
| Diethylene Glycol | 11 |
| Triethylene Glycol | 18 |
| Polyethylene Glycol 200 Molecular Weight | 16 |
| Polyethylene Glycol 400 Molecular weight | 31 |
| Polyethylene Glycol 600 Molecular Weight | 29 |
| Polyethylene Glycol 1000 Molecular Weight | 31 |
| Methoxy Polyethylene Glycol 350 Molecular Weight | 28 |
| Methoxy Polyethylene Glycol 550 Molecular Weight | 28 |
| Tetraglyme | 81 |
| Dipropylene Glycol | 13 |
| Tripropylene Glycol | 31 |
| Polypropylene Glycol 425 Molecular Weight | 76 |

EXAMPLE II

The compositions of Table I which were effective in reducing glutaraldehyde vaporization were tested by the A.O.A.C. Sporicidal Test to determine the sporicidal activity against B. subtilis spores on silk suture loops. The concentrations of glutaraldehyde and the identified compound were the same as in Example I. Each of the samples were aged for seven days at 40° C. and were then activated at a pH of 7.5 by the addition of 0.6% dipotassium phosphate. The results are reported in Table II.

TABLE II
Effect of Molecular Structure on Sporicidal Activity

| Compound | Sporicidal Activity # Failure/# Tested |
|---|---|
| None | 0/30 |
| Ethylene Glycol | 16/30 |
| 1,2 - Propylene Glycol | 11/30 |
| 1,3 - Propylene Glycol | 30/30 |
| 1,2 - Butanediol | 30/30 |
| 1,3 - Butanediol | 30/30 |
| 1,4 - Butanediol | 8/30 |
| 1,5 - Pentanediol | 6/30 |
| Glycerin | 29/30 |
| Sorbitol | 30/30 |
| Diethylene Glycol | 0/30 |
| Triethylene Glycol | 0/30 |
| Polyethylene Glycol 200 Molecular Weight | 0/30 |
| Polyethylene Glycol 400 Molecular Weight | 0/30 |
| Polyethylene Glycol 600 Molecular Weight | 0/30 |
| Polyethylene Glycol 1000 Molecular Weight | 0/30 |
| Methoxy Polyethylene Glycol 350 Molecular Weight | 0/30 |
| Methoxy Polyethylene Glycol 550 Molecular Weight | 0/30 |
| Dipropylene Glycol | 5/30 |
| Tripropylene Glycol | 3/30 |

EXAMPLE III

A 2.5% glutaraldehyde solution aged and activated as set forth in Example I was tested for glutaraldehyde vaporization with varying percentages of diol additive. Glutaraldehyde vaporization was reduced with as little as 5% of the additive. Increasing the concentration of the additive to 30% diol did not significantly decrease glutaraldehyde vaporization over that obtained at a 20% concentration of additive. The results are reported in Table III.

TABLE III

| | % Glutaraldehyde Vaporization % Additive | | | | |
|---|---|---|---|---|---|
| Additive | 0.0% | 5% | 10% | 20% | 30% |
| Polyethylene Glycol Molecular Weight 200 | 100 | 51 | 23 | 16 | 17 |
| Methoxy Polyethylene Glycol Molecular Weight 550 | 100 | — | 54 | 28 | 38 |

EXAMPLE IV

This example shows that the additives in the present composition are effective in reducing the glutaraldehyde vaporization at both an acid and alkaline pH. A glutaraldehyde solution was aged and activated as set forth in Example I. A polyethylene glycol having a molecular weight of 200 was added to one portion of the solution and each portion of the solution was tested for glutaraldehyde vaporization. The results are given in Table IV.

TABLE IV

| pH Effect on Glutaraldehyde Vaporization | | |
|---|---|---|
| | % Glutaraldehyde Vaporization | |
| Solution | pH 4.0 | pH 7.5 |
| 2.5% Glutaraldehyde | 99 | 100 |
| 2.5% Glutaraldehyde + 20% Polyethylene Glycol | 17 | 16 |

EXAMPLE V

The solutions set forth in Table IV were tested for percent glutaraldehyde vaporization at 25° C. and at 40° C. The results are set forth in Table V. The results show that the present additives are effective in reducing glutaraldehyde vaporization at elevated temperatures as well as at room temperature.

TABLE V

| Effect of Temperature on Rate of Glutaraldehyde Vaporization | | |
|---|---|---|
| | % Glutaraldehyde Vaporization Temperature | |
| Solution | 25° C. | 40° C. |
| 2.5% Glutaraldehyde | 100 | 149 |
| 2.5% Glutaraldehyde + 20% Polyethylene Glycol | 16 | 48 |

EXAMPLE VI

This Example shows that the diols of the present invention will reduce the aldehyde vaporization of formaldehyde alone or in combination with a dialdehyde. (The test for the formaldehyde vaporization is the same test used for glutaraldehyde vaporization.) A series of aqueous solutions containing the aldehyde and diol indicated in Table VI were prepared. Each solution was aged for 7 days at 40° C. prior to activation to pH 7.5 with 1.7% potassium acetate and 0.6% dipotassium phosphate. The solutions were tested for aldehyde vaporization, and the results were reported in Table VI.

TABLE VI

| Aldehyde Type Effect | | |
|---|---|---|
| | % Aldehyde Vaporization | |
| Solution | Formaldehyde (%) | Glutaraldehyde (%) |
| 2.5% Formaldehyde | 100 | — |

TABLE VI-continued

| Aldehyde Type Effect | | |
|---|---|---|
| | % Aldehyde Vaporization | |
| Solution | Formaldehyde (%) | Glutaraldehyde (%) |
| 2.5% Formaldehyde + 20% Polyethylene Glycol 200 m.w. | 49 | — |
| 2.5% Formaldehyde + 2.5% Glutaraldehyde | 100 | 100 |
| 2.5% Formaldehyde + 2.5% Glutaraldehyde + 20% Polyethylene Glycol 200 m.w. | 60 | 16 |

The results of this test demonstrate that polyethylene glycol will (1) significantly reduce the rate of vaporization of formaldehyde, a very volatile monoaldehyde, and (2) reduce the vaporization rate of a mixture of glutaraldehyde with formaldehyde.

EXAMPLE VII

A series of solutions containing 0.2% and 0.4% by weight, based on the total weight of the solution glutaraldehyde combined with 5%, 10% and 20% by weight of a diol which was polyethylene glycol having a molecular weight of 200. A control containing no glutaraldehyde was also prepared. Each solution contained 1.7% potassium acetate and 0.6% dipotassium phosphate. The formulations had a pH of from 7.57 to 7.9. The formulations were tested in a A.O.A.C. Use-Dilution Test using 30 replicates per formulation against staphylococcus aureus, pseudomonas aeruginosa and salmonella choleraesuis. Letheen both was the subculture and resubculture medium. The exposure time was 10 minutes at 20° C. for all tests. The results are given in Table VII.

TABLE VII

| | | Bactericidal Activity # Failures/# Tested | | |
|---|---|---|---|---|
| Formulation | Components Tested | S. Aureus | P. Aeruginosa | S. Choleraesuis |
| 1 | 0.2% glutaraldehyde, 5% diol | 2/30 | 1/30 | 0/30 |
| 2 | 0.2% glutaraldehyde, 10% diol | 2/30 | 4/30 | 2/30 |
| 3 | 0.2% glutaraldehyde, 20% diol | 0/30 | 1/30 | 1/30 |
| 4 | 0.2% glutaraldehyde, No diol | 1/30 | 0/30 | 0/30 |
| 5 | 0.4% glutaraldehyde, 5% diol | 0/30 | 0/30 | 0/30 |
| 6 | 0.4% glutaraldehyde, 10% diol | 0/30 | 1/30 | 0/30 |
| 7 | 0.4% glutaraldehyde, 20% diol | 0/30 | 0/30 | 2/30 |
| 8 | 0.4% glutaraldehyde, No diol | 1/30 | 1/30 | 1/30 |
| 9 | No glutaraldehyde, 20% diol | 30/30 | 30/30 | 30/30 |

The data in Table VII indicates no appreciable differences in bactericidal activity at the indicated levels of glutaraldehyde and polyethylene glycol. The control showed that the polyethylene glycol has no antimicrobial activity.

The following Examples VIII and IX show the effect of the presence of phenol in a sterilizing composition on the vaporization of glutaraldehyde.

EXAMPLE VIII

A series of solutions were prepared which contained glutaraldehyde and either diethylene glycol or a polyethylene glycol of a molecular weight of 200. Phenol and sodium phenolate were added in different amounts, and the glutaraldehyde vaporization was determined. All the solutions also contain 0.6% dipotassium phosphate and 1.7% potassium acetate as the activator. All solutions were pH 7.5. All percentages are by weight. The results are shown in Table VIII.

TABLE VIII

Effect of Phenol/Phenolate On Vaporization of Glutaraldehyde

| Solution* | Glutaraldehyde Vaporization ($\mu$g Glut.) | (%) Increase |
|---|---|---|
| 2.5% Glut. + 20% Diethylene Glycol | 28.9 | — |
| 2.5% Glut. + 20% Diethylene Glycol (3.0% Phenol + 0.5% Sodium Phenolate) | 39.6 | 37 |
| 2.5% Glut. + 20% Diethylene Glycol (10% Phenol + 5.0% Sodium Phenolate) | 37.0 | 28 |
| 2.5% Glut. + 20% Polyethylene Glycol | 47.6 | — |
| 2.5% Glut. + 20% Polyethylene Glycol (3.0% Phenol + 0.5% Sodium Phenolate) | 51.8 | 10 |
| 2.5% Glut. + 20% Polyethylene Glycol (10% Phenol + 5.0% Sodium Phenolate) | 70.8 | 48 |

EXAMPLE IX

The procedure set forth in Example VIII was repeated, but the samples were aged for 7 days at 40° C. The samples were then activated and tested. The results are reported in Table IX.

TABLE IX

Effect of Phenol/Phenolate On Vaporization of Glutaraldehyde

| Solution* | Glutaraldehyde Vaporization ($\mu$g Glut.) | (%) Increase |
|---|---|---|
| 2.5% Glut. + 20% Diethylene Glycol | 54 | — |
| 2.5% Glut. + 20% Diethylene Glycol (3.0% Phenol + 0.5% Sodium Phenolate) | 68 | 26 |
| 2.5% Glut. + 20% Diethylene Glycol (10% Phenol + 5.0% Sodium Phenolate) | 63 | 17 |
| 2.5% Glut. + 20% Polyethylene Glycol | 75 | — |
| 2.5% Glut. + Polyethylene Glycol (3.0% Phenol + 0.5% Sodium Phenolate) | 76 | 1.3 |
| 2.5% Glut. + 20% Polyethylene Glycol (10.0% Phenol + 5.0% Sodium Phenolate) | 93 | 24 |

I claim:

1. A phenol-free sporicidal composition having low odor and irritation potential comprising an aqueous solution containing 0.1% to 4% by weight of a 2 to 6 carbon atom saturated dialdehyde and containing as an odor reducing agent 5% to 25% by weight of a diol or monosubstituted diol of the formula RO(CH$_2$CH$_2$O)$_n$—CH$_2$CH$_2$OH, where R is H or CH$_3$— and n is an integer from 1 to about 22.

2. A composition of claim 1 having a pH of from 7 to 9 and where R is H.

3. A composition of claim 2 in which the dialdehyde is present in an amount of from 2 to 3% based on the weight of the solution, and the diol is present in an amount of from 10% to 20% based on the weight of the solution.

4. A composition of claim 2 in which the solution also contains from 0.1 to 3% based on the weight of the solution of formaldehyde.

5. The composition of claim 1 in which the saturated dialdehyde is glutaraldehyde.

6. The composition of claim 5 in which R is H and the diol has a molecular weight of 200.

7. The composition of claim 1 in which R is H and n is 3.

8. The composition of claim 1 in which R is CH$_3$.

9. The composition of claim 1 additionally containing 0.6% to 2.5% by weight of a pH buffer salt selected from the group consisting of alkali metal carbonates, alkali metal bicarbonates, alkali metal phosphates, alkali metal borates, organic carboxylate salts and mixtures thereof.

10. The composition of claim 1 in which the diol or substituted diol has a molecular weight of from 200 to 600.

* * * * *